United States Patent
Fukuzawa

(10) Patent No.: US 12,186,756 B2
(45) Date of Patent: Jan. 7, 2025

(54) REACTION PROCESSOR

(71) Applicant: Go!Foton, Inc., Tsukuba (JP)

(72) Inventor: Takashi Fukuzawa, Machida (JP)

(73) Assignee: Go!Foton, Inc., Tsukuba (JP)

( * ) Notice: Subject to any disclaimer, the term of this patent is extended or adjusted under 35 U.S.C. 154(b) by 924 days.

(21) Appl. No.: 17/243,770

(22) Filed: Apr. 29, 2021

(65) Prior Publication Data

US 2021/0245162 A1 Aug. 12, 2021

Related U.S. Application Data

(63) Continuation of application No. 16/431,841, filed on Jun. 5, 2019, now Pat. No. 11,020,746, which is a (Continued)

(30) Foreign Application Priority Data

Dec. 6, 2016 (JP) ................................. 2016-236597

(51) Int. Cl.
B01L 7/00 (2006.01)
B01L 3/00 (2006.01)
(Continued)

(52) U.S. Cl.
CPC .............. *B01L 7/52* (2013.01); *B01L 3/5027* (2013.01); *B01L 7/525* (2013.01); *B01L 7/54* (2013.01);
(Continued)

(58) Field of Classification Search
None
See application file for complete search history.

(56) References Cited

U.S. PATENT DOCUMENTS 6,369,928 B1 4/2002 Mandella et al.
2007/0292941 A1 12/2007 Handique et al.
(Continued)

FOREIGN PATENT DOCUMENTS

GB 2472454 A 2/2011
JP 2009-531064 A 9/2009
(Continued)

OTHER PUBLICATIONS

Fukuzawa, Takashi et al., "Development on commercialization of rapid quantification device for pathogenic microorganisms in environment", Development of Advanced Measurement and Analysis Systems, Apr. 2016, p. 23 (2 pages total).
(Continued)

*Primary Examiner* — Paul S Hyun
*Assistant Examiner* — Jean C. Caraballo-Leon
(74) *Attorney, Agent, or Firm* — Sughrue Mion, PLLC

(57) ABSTRACT

A reaction processor includes: a vessel installation unit for installing a reaction processing vessel provided with a channel formed in a substrate; a high temperature heater and a medium temperature heater for adjusting the temperature of the channel of the reaction processing vessel; a vessel alignment mechanism for adjusting the position of the reaction processing vessel 10; and a housing that has a housing main unit and a cover portion capable of being opened and closed with respect to the housing main unit and that houses the vessel installation unit, the high temperature heater, the medium temperature heater, and the vessel alignment mechanism. In conjunction with the state of the cover portion being changed from an open state to a closed state, the vessel alignment mechanism aligns the reaction processing vessel such that the reaction processing vessel can be heated by the high temperature heater and the medium temperature heater.

5 Claims, 15 Drawing Sheets

Related U.S. Application Data continuation of application No. PCT/JP2017/042037, filed on Nov. 22, 2017.

(51) Int. Cl.
    *C12M 1/00*     (2006.01)
    *C12M 1/34*     (2006.01)
    *C12N 15/09*     (2006.01)
    *C12Q 1/6844*     (2018.01)
    *C12Q 1/686*     (2018.01)

(52) U.S. Cl.
    CPC ............... *C12M 1/00* (2013.01); *C12M 1/34* (2013.01); *B01L 2200/10* (2013.01); *B01L 2300/0816* (2013.01); *B01L 2300/0883* (2013.01); *B01L 2300/123* (2013.01); *B01L 2300/1805* (2013.01); *B01L 2400/04* (2013.01); *C12N 15/09* (2013.01); *C12Q 1/6844* (2013.01); *C12Q 1/686* (2013.01)

(56) References Cited

U.S. PATENT DOCUMENTS

| | | | |
|---|---|---|---|
| 2015/0132860 A1 | 5/2015 | Cook et al. | |
| 2015/0137015 A1 | 5/2015 | Toh et al. | |
| 2015/0267695 A1 | 9/2015 | Marsh | |
| 2015/0346097 A1 | 12/2015 | Battrell et al. | |
| 2016/0016171 A1 | 1/2016 | Goel | |

FOREIGN PATENT DOCUMENTS

| | | | |
|---|---|---|---|
| JP | 2009-232700 A | 10/2009 | |
| WO | 2016006612 A1 | 1/2016 | |

OTHER PUBLICATIONS

International Preliminary Report on Patentability with a Translation of Written Opinion in International Application No. PCT/JP2017/042037, dated on Jun. 20, 2019.

International Search Report in International Application No. PCT/JP2017/042037, issued on Feb. 27, 2018.

Japan Science and Technology Agency, et al., "Success in developing mobile gene testing device—, being brought to field and detecting bacteria and virus for about 10 minutes—", Feb. 2017, pp. 1-7 (11 pages total).

Anonymous, "Orthogonal Definition", Lexico.com., Retrieved Oct. 2019, (1 page total).

Anonymous, "Longitudinal Definition", Lexico.com., Retrieved Oct. 2019, (1 page total).

Notification of Reasons for Refusal dated Sep. 7, 2021 from the Japanese Patent Office in JP application No. 2018-554918.

REACTION PROCESSOR

CROSS-REFERENCE TO RELATED APPLICATIONS

The present application is a continuation of U.S. application Ser. No. 16/431,841 filed Jun. 5, 2019, which is a Continuation of International Application No. PCT/JP2017/042037, filed Nov. 22, 2017, claiming priority based on Japanese Patent Application No. 2016-236597 filed Dec. 6, 2016, the contents of all of which are incorporated herein by reference in their entirety.

BACKGROUND OF THE INVENTION

1. Field of the Invention

The present invention relates to reaction processors used for polymerase chain reactions (PCR).

2. Description of the Related Art

Genetic testing is widely used for examinations in a wide variety of medical fields, identification of farm products and pathogenic microorganisms, safety assessment for food products, and even for examinations for pathogenic viruses and a variety of infectious diseases. In order to detect with high sensitivity a minute amount of gene's DNA, methods of analyzing the resultant obtained by amplifying a portion of DNA are known. Above all, a method that uses PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause denaturation, annealing, and elongation reactions to be repeated so that a specific portion of DNA is selectively amplified.

It is a common practice to perform PCR by putting a predetermined amount of a target sample into a PCR tube or a reaction processing vessel such as a microplate (microwell) in which a plurality of holes are formed. However, in recent years, PCR using a reaction processing vessel (also referred to as "chip") provided with a micro-channel that is formed on a substrate is practiced (e.g. Patent Document 1).

[Patent Document 1] JP 2009-232700

SUMMARY OF THE INVENTION

In a reaction processor in which a reaction processing vessel such as the one described above is used, from the viewpoint of workability, the reaction processing vessel is preferably set in a short time inside a housing that houses components such as a heater and a pump so as to be able to start a reaction process including PCR.

In this background, a purpose of the present invention is to provide a reaction processor capable of improving the workability in a reaction process including PCR.

A reaction processor according to one embodiment of the present invention includes: a vessel installation unit for installing a reaction processing vessel provided with a channel formed in a substrate; a heater for adjusting the temperature of the channel of the reaction processing vessel; a vessel alignment mechanism for adjusting the position of the reaction processing vessel; and a housing that has a housing main unit and a cover portion capable of being opened and closed with respect to the housing main unit and that houses the vessel installation unit, the heater, and the vessel alignment mechanism. In conjunction with the state of the cover portion being changed from an open state to a closed state, the vessel alignment mechanism aligns the reaction processing vessel such that the reaction processing vessel can be heated by the heater.

The reaction processor may further include an elastic member that allows the reaction processing vessel to be in close contact with the heater when the cover portion is in the closed state.

The channel may include a first temperature region maintained at a first temperature and a second temperature region maintained at a second temperature that is higher than the first temperature in order to apply a thermal cycle to a sample. The heater may include a first heater for heating the first temperature region of the channel and a second heater for heating the second temperature region of the channel.

In the housing main unit, a pump that adjusts the pressure inside the channel of the reaction processing vessel may be further included in order to move and stop the sample inside the channel. A tube extending from the pump may communicate with the channel of the reaction processing vessel when the state of the cover portion is changed from the open state to the closed state.

The pump may include a first pump having a first tube and a second pump having a second tube. The first tube may be connected to a first air communication port formed at one end of the channel and the second tube may be connected to a second air communication port formed at the other end of the channel when the state of the cover portion is changed from the open state to the closed state.

In the housing main unit, a fluorescence detector for detecting fluorescence emitted from the sample inside the channel may be further included. A predetermined fluorescence detection point of the reaction processing vessel may be aligned with the fluorescence detector when the state of the cover portion is changed from the open state to the closed state.

The fluorescence detector may be an optical fiber-type fluorescence detector in which an optical head and a driver including a light source for excitation light, multiplexer/demultiplexer, and a photoelectric conversion device are connected by an optical fiber.

The reaction processor described above may be formed to be portable.

BRIEF DESCRIPTION OF THE DRAWINGS

Embodiments will now be described, byway of example only, with reference to the accompanying drawings which are meant to be exemplary, not limiting, and wherein like elements are numbered alike in several Figures, in which.

DETAILED DESCRIPTION OF THE INVENTION

Figure 1A:
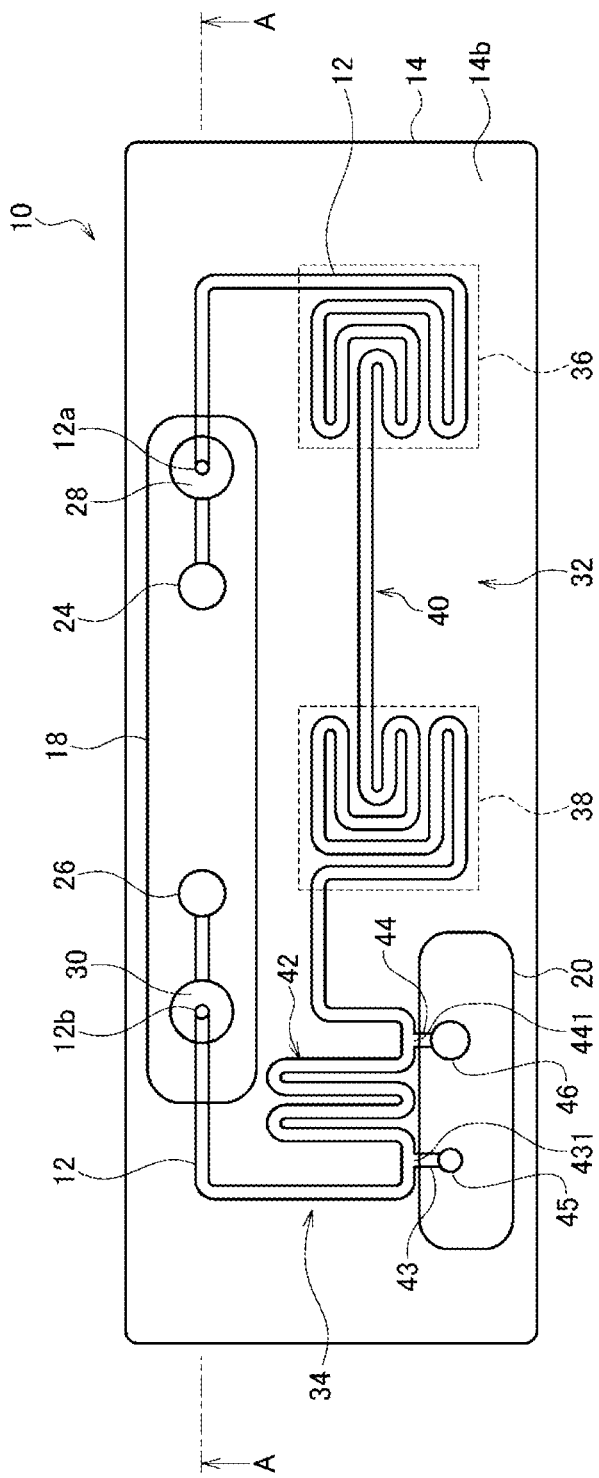
FIGS. 1A and 1B are diagrams for explaining a reaction processing vessel usable in a reaction processor according to an embodiment of the present invention.

An explanation will be given in the following regarding a reaction processing vessel and a reaction processor according to an embodiment of the present invention. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and all the features described in the embodiments and combinations thereof are not necessarily essential to the invention.

Figure 1B:
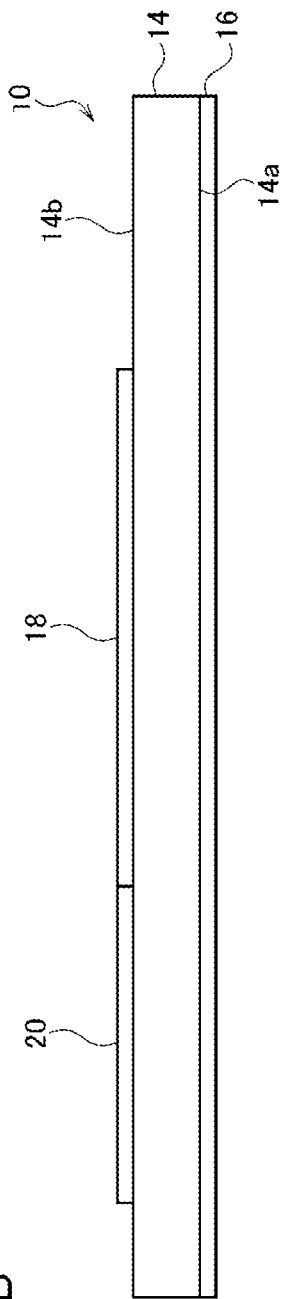
Figure 2:
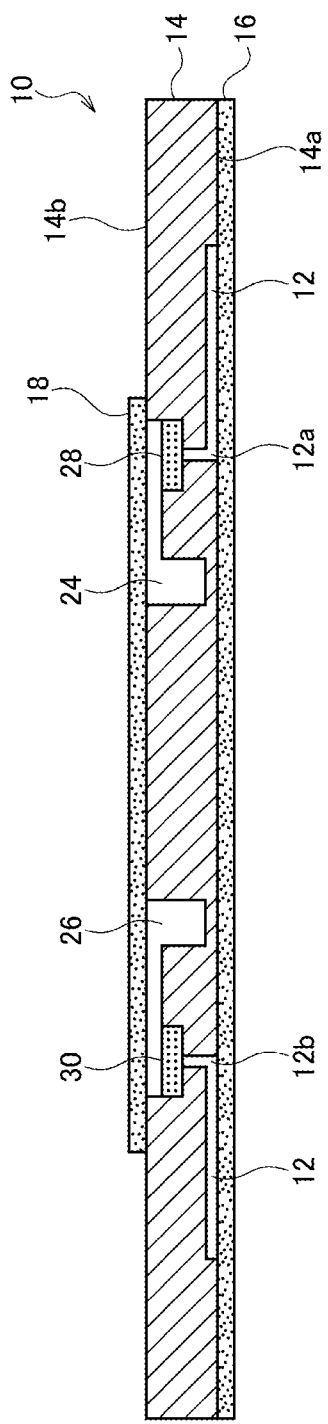
FIG. 2 is a cross-sectional view of the reaction processing vessel shown in FIG. 1A that is sectioned along line A-A.
Figure 3:
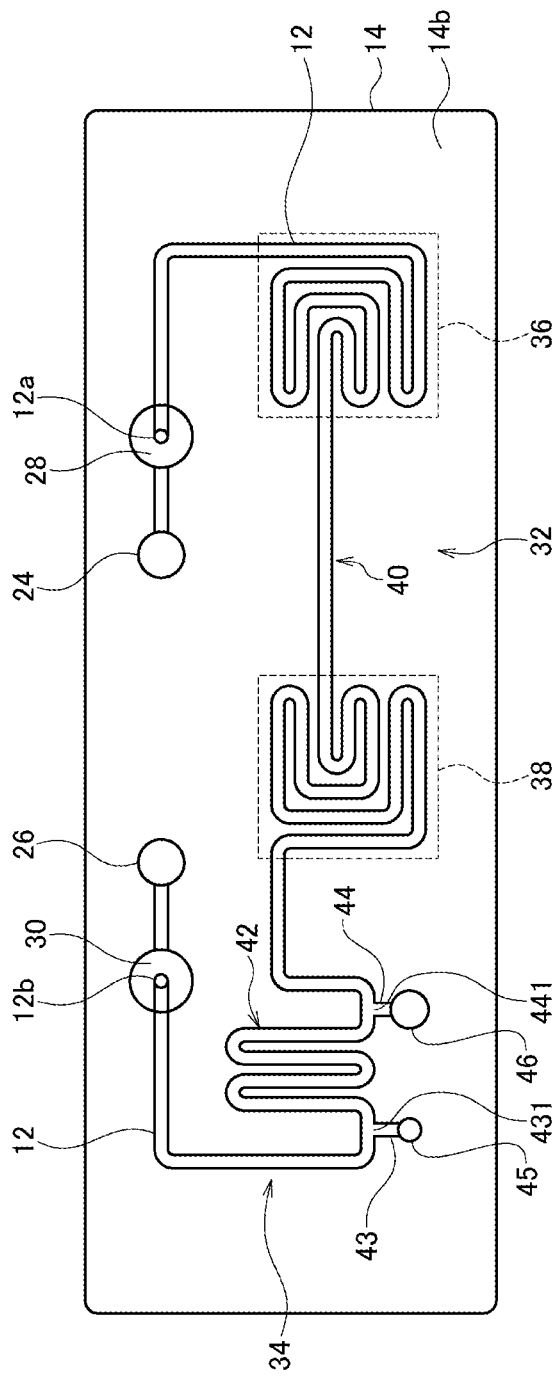
FIG. 3 is a plan view of a substrate provided in the reaction processing vessel.

FIGS. 1A and 1B are diagrams for explaining a reaction processing vessel 10 usable in a reaction processor according to an embodiment of the present invention. FIG. 1A is a plan view of the reaction processing vessel 10, and FIG. 1B is a front view of the reaction processing vessel 10. FIG. 2 is a cross-sectional view of the reaction processing vessel 10 shown in FIG. 1A that is sectioned along line A-A. FIG. 3 is a plan view of a substrate 14 provided in the reaction processing vessel 10.

The reaction processing vessel 10 comprises a resinous substrate 14 having a groove-like channel 12 formed on a lower surface 14a thereof, a channel sealing film 16, which is attached on the lower surface 14a of the substrate 14, for sealing the channel 12, and two sealing films (a first sealing film 18 and a second sealing film 20) attached on an upper surface 14b of the substrate 14.

The substrate 14 is preferably formed of a material that is stable under temperature changes and is resistant to a sample solution that is used. Further, the substrate 14 is preferably formed of a material that has good moldability, a good transparency and barrier property, and a low self-fluorescent property. As such a material, an inorganic material such as glass, silicon (Si), or the like, a resin such as acrylic, polyester, silicone, or the like, and particularly a cycloolefin polymer resin (COP) are preferred. An example of the dimensions of the substrate 14 includes a long side of 76 mm, a short side of 26 mm, and a thickness of 4 mm.

The groove-like channel 12 is formed on the lower surface 14a of the substrate 14. In the reaction processing vessel 10, most of the channel 12 is formed in the shape of a groove exposed on the lower surface 14a of the substrate 14. This is for allowing for easy molding through injection molding using a metal mold or the like. In order to seal this groove so as to make use of the groove as a channel, the channel sealing film 16 is attached on the lower surface 14a of the substrate 14. An example of the dimensions of the channel 12 includes a width of 0.7 mm and a depth of 0.7 mm.

The channel sealing film 16 may be sticky on one of the main surfaces thereof or may have a functional layer that exhibits stickiness or adhesiveness through pressing, energy irradiation with ultraviolet rays or the like, heating, etc., formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescent property. In this respect, a transparent film made of a resin such as a cycloolefin polymer, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

A first air communication port 24 is formed at the position of one end 12a of the channel 12 in the substrate 14. A second air communication port 26 is formed at the position of the other end 12b of the channel 12 in the substrate 14. The pair, the first air communication port 24 and the second air communication port 26, is formed so as to be exposed on the upper surface 14b of the substrate 14.

A first filter 28 is provided between the first air communication port 24 and one end 12a of the channel 12 in the substrate 14. A second filter 30 is provided between the second air communication port 26 and the other end 12b of the channel 12 in the substrate 14. The pair, the first filter 28 and the second filter 30, provided at respective ends of the channel 12, has good low impurity characteristics and also allows only air to pass therethrough so as to prevent contamination so that the amplification of target DNA and the detection of the amplification are not interrupted by PCR or so that the quality of the target DNA does not deteriorate. As a filter material, for example, a material obtained by subjecting polyethylene to a water repellent treatment can be used. Alternatively, a known material can be selected as long as the material has the above function. Regarding the dimensions of the first filter 28 and the second filter 30, the first filter 28 and the second filter 30 are formed so as to fit without any gap in a filter installation space formed in the substrate 14 and may have, for example, a diameter of 4 mm and a thickness of 2 mm.

As shown in FIG. 1A, between the pair consisting of the first air communication port 24 and the second air communication port 26, the channel 12 includes a thermal cycle region 32 for applying a thermal cycle to the sample and a dispensing region 34 for performing so-called dispensing where a predetermined amount of the sample is extracted. The thermal cycle region 32 is located on the side of the first air communication port 24 in the channel 12. The dispensing region 34 is located on the side of the second air communication port 26 in the channel 12. The thermal cycle region 32 and the dispensing region 34 communicate with each other. By moving the sample dispensed in the dispensing region 34 to the thermal cycle region 32 such that the sample continuously reciprocates between reaction regions maintained at a predetermined temperature that are included in the thermal cycle region 32, a thermal cycle can be applied to the sample.

When the reaction processing vessel 10 is mounted on a reaction processor described later, the thermal cycle region 32 of the channel 12 includes a reaction region (hereinafter referred to as "medium temperature region 38") maintained at a relatively low temperature (about 60° C.), a reaction region (hereinafter referred to as "high temperature region 36") maintained at a higher temperature (about 95° C.), and a connection region 40 connecting the high temperature region 36 and the medium temperature region 38. The high temperature region 36 is located on the side of the first air communication port 24, and the medium temperature region 38 is located on the side of the second air communication port 26 (in other words, on the dispensing region 34 side).

The high temperature region 36 and the medium temperature region 38 each include a serpiginous shape channel where a turn is continuously made by combining curved portions and straight portions. Ina case where a serpiginous shape channel is used as described above, an effective area that is limited such as that of a heater or the like constituting a temperature control means described later can be effectively used, and there are advantages that temperature variance in the reaction region is easily reduced and that the substantial size of the reaction processing vessel can be reduced, contributing to the downsizing of the reaction processor. The connection region 40 may be a linear channel.

The dispensing region 34 of the channel 12 is located between the medium temperature region 38 in the thermal cycle region 32 and the second filter 30. As described above, the dispensing region 34 has a dispensing function of extracting a predetermined amount of the sample to be subjected to PCR. The dispensing region 34 includes a dispensing channel 42 for defining a predetermined amount of the sample, two branch channels (a first branch channel 43 and a second branch channel 44) branching from the dispensing channel 42, a first sample introduction port 45 arranged at an end of the first branch channel 43, and a second sample introduction port 46 arranged at an end of the second branch channel 44. The first sample introduction port 45 communicates with the dispensing channel 42 via the first branch channel 43. The second sample introduction port 46 communicates with the dispensing channel 42 via the second branch channel 44. The dispensing channel 42 is a serpiginous shape channel in order to dispense a predetermined amount of the sample using a minimum area. The first sample introduction port 45 and the second sample introduction port 46 are formed so as to be exposed on the upper surface 14b of the substrate 14. The first sample introduction port 45 is formed to have a comparatively small diameter, and the second sample introduction port 46 is formed to have a relatively large diameter. When a branch point at which the first branch channel 43 branches from the dispensing channel 42 is defined as a first branch point 431 and a branch point at which the second branch channel 44 branches from the dispensing channel 42 is defined as a second branch point 441, the volume of the sample to be subjected to PCR is almost determined by the volume inside the dispensing channel 42 between the first branch point 431 and the second branch point 441.

In the reaction processing vessel 10, the dispensing region 34 is provided between the thermal cycle region 32 and the second filter 30. However, the position of the dispensing region 34 is not limited to this, and the dispensing region 34 may be provided between the thermal cycle region 32 and the first filter 28. As long as the dispensing can be done accurately using a pipette or the like, the channels may be formed without providing the dispensing region 34 or formed such that the sample can be introduced directly into the thermal cycle region 32 or the like.

The first air communication port 24, the second air communication port 26, the first filter 28, the second filter 30, the first sample introduction port 45, and the second sample introduction port 46 are exposed on the upper surface 14b of the substrate 14. Therefore, in order to seal the first air communication port 24, the second air communication port 26, the first filter 28, and the second filter 30, the first sealing film 18 is attached to the upper surface 14b of the substrate 14. In order to seal the first sample introduction port 45 and the second sample introduction port 46, the second sealing film 20 is attached to the upper surface 14b of the substrate 14. In a state where the first sealing film 18 and the second sealing film 20 are attached, the entire channel forms a closed space.

The first sealing film 18 that is used has a size that allows the first air communication port 24, the second air communication port 26, the first filter 28, and the second filter 30 to be sealed at the same time. A pressure-type pump (described later) is connected to the first air communication port 24 and the second air communication port 26 by perforating the respective parts of the first sealing film 18 that correspond to the first air communication port 24 and the second air communication port 26 by a hollow needle (syringe needle with a sharp tip) provided at the tip of the pump. Therefore, the first sealing film 18 is preferably a film made of a material that is easily perforated by the needle and/or have a thickness that is easily perforated by the needle. In the reaction processing vessel 10, the sealing film having a size that is capable of sealing the first air communication port 24, the second air communication port 26, the first filter 28, and the second filter 30 at the same time is described. However, these air communication ports and filters may be sealed separately. Further, the film sealing the first air communication port 24 and the second air communication port 26 may be peeled off so as to be connected to a pressure-type pump.

As the second sealing film 20, a sealing film having a size that is capable of sealing the first sample introduction port 45 and the second sample introduction port 46 is used. Introduction of a sample into the channel 12 through the first sample introduction port 45 and the second sample introduction port 46 is performed by once peeling the second sealing film 20 from the substrate 14, and, after the introduction of a predetermined amount of sample, the second sealing film 20 is put back being attached to the upper surface 14b of the substrate 14 again. Therefore, as the second sealing film 20, a film is desired that is sticky enough to hold up through several cycles of attaching and peeling. Alternatively, as the second sealing film 20, a new film may be attached after the introduction of a sample. In this case, the importance of the property related to repetitive attaching and peeling can be lessened.

In the same way as in the channel sealing film 16, the first sealing film 18 and the second sealing film 20 may have an adhesive layer or a functional layer exhibiting stickiness or adhesiveness by pressing that is formed on one of the main surfaces thereof. In this respect, a transparent film made of a resin such as a cycloolefin polymer, polyester, polypropylene, polyethylene or acrylic is suitable but is not limited thereto. As described above, the property such as stickiness or the like desirably do not degrade to such an extent that the use is affected even after attaching and peeling of multiple times. However, in a case where a new film is attached after the peeling and the introduction of a sample or the like or after the connection to a pressure-type pump, the importance of this property related to the attaching and peeling can be lessened.

An explanation will be given next regarding a method of using the reaction processing vessel 10 formed as described above. First, a sample to be amplified through a thermal cycle is prepared. The sample includes, for example, those obtained by adding a fluorescent probe, a thermostable enzyme and four types of deoxyribonucleoside triphosphates (dATP, dCTP, dGTP, dTTP) as PCR reagents to a mixture containing one or more types of DNA. Further, a primer that specifically reacts to DNA subjected to a reaction process is mixed. Commercially available real-time PCR reagent kits and the like can be also used.

Next, the second sealing film 20 is peeled off from the substrate 14 such that the first sample introduction port 45 and the second sample introduction port 46 are open.

Figure 4:
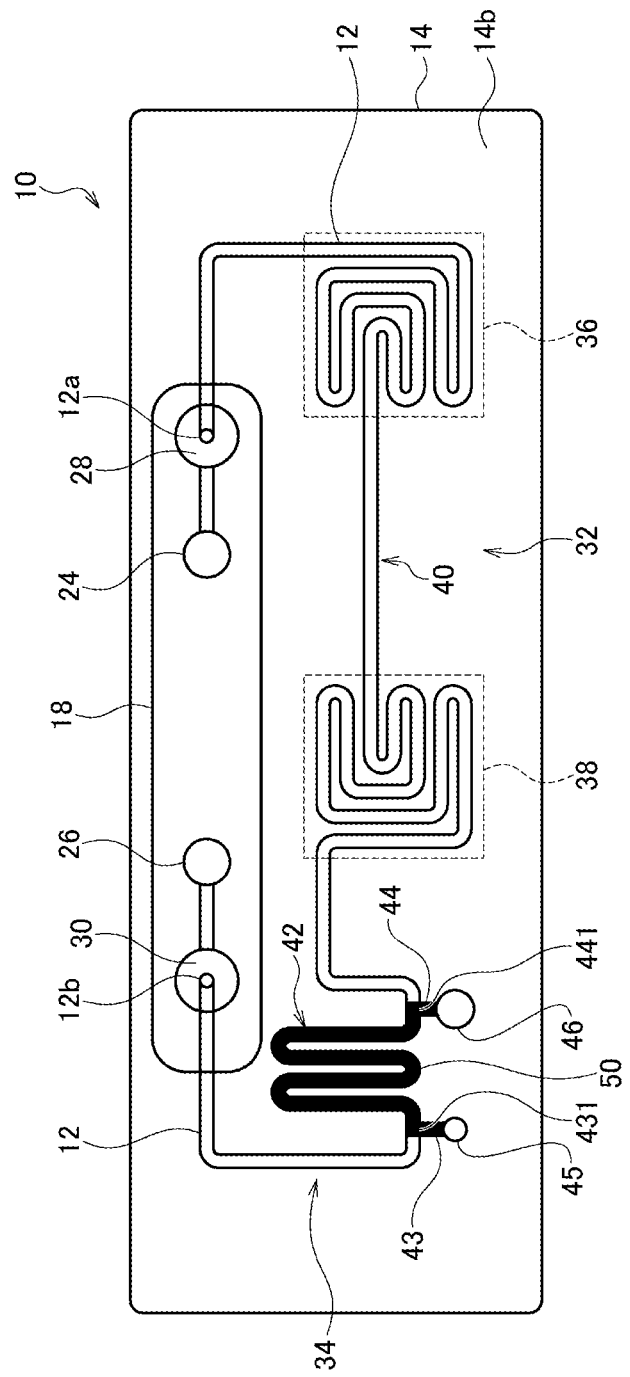
FIG. 4 is a diagram schematically showing a state where a sample is introduced into the reaction processing vessel.

The sample is then introduced to a sample introduction port by a dropper, a syringe, or the like. FIG. 4 schematically shows a state where a sample 50 is introduced into the reaction processing vessel 10. The sample 50 is introduced into the dispensing channel 42 through either one of the first sample introduction port 45 and the second sample introduction port 46. The method for the introduction is not limited to this. Alternatively, for example, an appropriate amount of the sample 50 may be directly introduced using a pipette or a dropper. When the sample is introduced using a pipette, the sample 50 is introduced through the first sample introduction port 45, which has a relatively small diameter. In this case, the sample 50 is loaded into the dispensing channel 42 toward the second sample introduction port 46. When the sample 50 is introduced using a dropper, the sample 50 is introduced through the second sample introduction port 46, which has a relatively large diameter. In this case, the sample 50 is loaded into the dispensing channel 42 toward the first sample introduction port 45. The excess portion of the sample introduced through either one of the sample introduction ports that exceeds the volume of the branch channel becomes accumulated at the other one of the sample introduction ports. Therefore, in order to utilize the sample introduction port part as a kind of server, the sample introduction port part may be made to have a certain space. As will be described later, the sample 50 loaded into the dispensing channel 42 between the first branch point 431 and the second branch point 441 undergoes PCR by pressurization from the first air communication port 24 and the second air communication port 26. In this manner, the dispensing region 34 of the reaction processing vessel 10 performs a dispensing function of extracting a predetermined amount of sample.

Next, the second sealing film 20 is attached to the substrate 14 again such that the first sample introduction port 45 and the second sample introduction port 46 are sealed. Instead of the second sealing film 20 that has been peeled off, a new second sealing film 20 may be attached. This completes the introduction of the sample 50 into the reaction processing vessel 10.

The above-mentioned dispensing function in the reaction processing vessel is not to prevent introduction of the sample while precisely dispensing the sample with a pipette alone.

Figure 5:
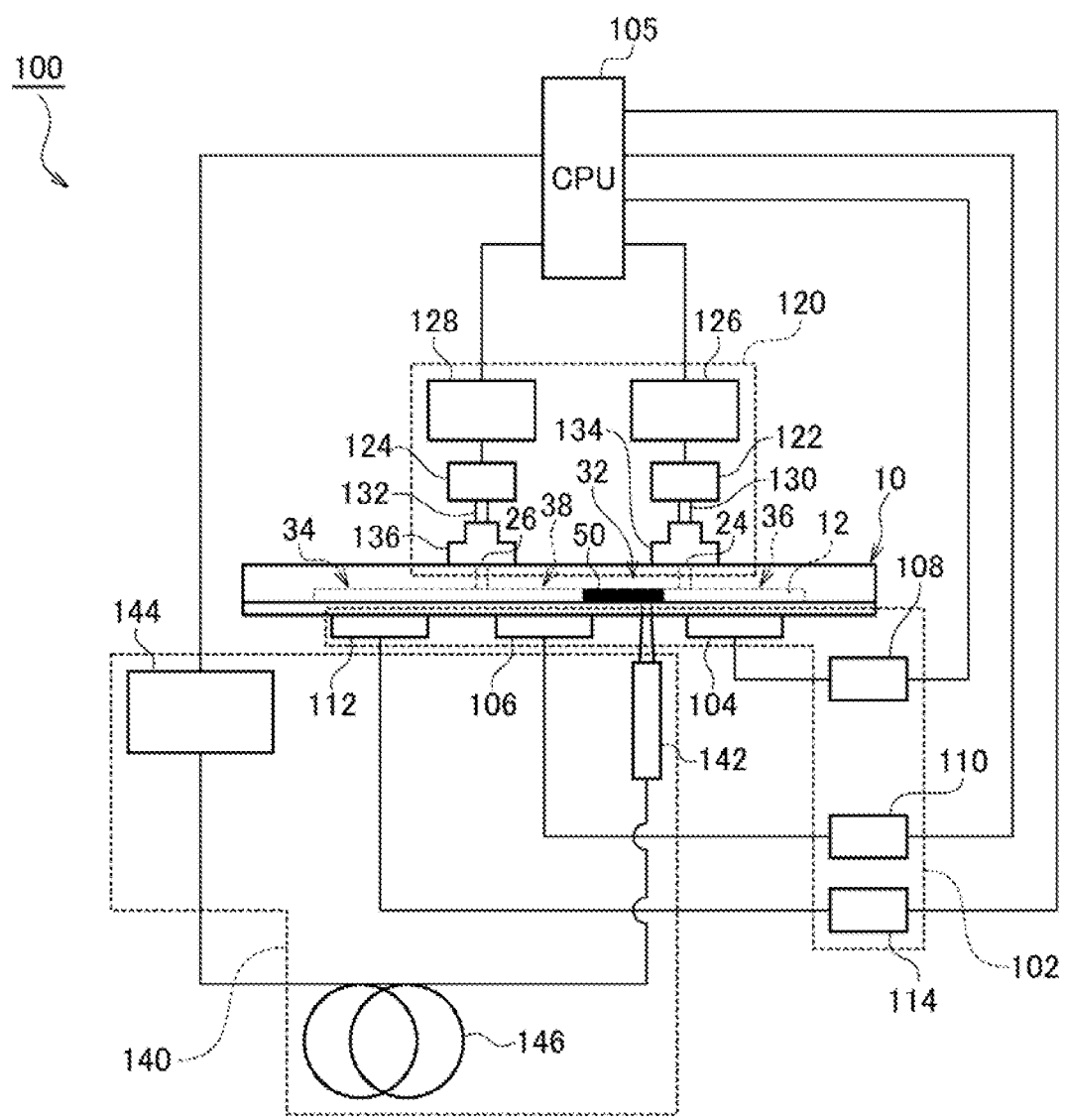
FIG. 5 is a schematic diagram for explaining a reaction processor according to an embodiment of the present invention.

FIG. 5 is a schematic diagram for explaining a reaction processor 100 according to the embodiment of the present invention.

The reaction processor 100 according to the present embodiment includes a vessel installation unit (not shown) in which the reaction processing vessel 10 is installed, a temperature control system 102, and a CPU 105. As shown in FIG. 5, relative to the reaction processing vessel 10 installed in the vessel installation unit, the temperature control system 102 is formed so as to be able to accurately maintain and control the temperature of the high temperature region 36 in the channel 12 of the reaction processing vessel 10 to be about 95° C. (high temperature region) and the temperature of the medium temperature region 38 to be about 60° C.

The temperature control system 102 is for adjusting the temperature of each temperature region of a thermal cycle region and is specifically provided with a high temperature heater 104 for heating the high temperature region 36 of the channel 12, a medium temperature heater 106 for heating the medium temperature region 38 of the channel 12, a temperature sensor (not shown) such as, for example, a thermocouple or the like for measuring the actual temperature of each temperature region, a high temperature heater driver 108 for controlling the temperature of the high temperature heater 104, and a medium temperature heater driver 110 for controlling the temperature of the medium temperature heater 106. Further, the reaction processor 100 according to the present embodiment includes a dispensing heater 112 for heating the dispensing region 34 of the channel 12 and a dispensing heater driver 114 for controlling the temperature of the dispensing heater 112. Information on the actual temperature measured by the temperature sensor is sent to the CPU 105. Based on the information on the actual temperature of each temperature region, the CPU 105 controls each heater driver such that the temperature of each heater becomes a predetermined temperature. Each heater may be, for example, a resistance heating element, a Peltier element, or the like. The temperature control system 102 may be further provided with other components for improving the temperature controllability of each temperature region.

The reaction processor 100 according to the present embodiment is further provided with a liquid feeding system 120 for moving and stopping the sample 50 inside the channel 12 of the reaction processing vessel 10. The liquid feeding system 120 is provided with a first pump 122, a second pump 124, a first pump driver 126 for driving the first pump 122, a second pump driver 128 for driving the second pump 124, a first tube 130, and a second tube 132.

One end of the first tube 130 is connected to the first air communication port 24 of the reaction processing vessel 10. A packing material 134 or a seal for securing airtightness is preferably arranged at the junction of the first air communication port 24 and the end of the first tube 130. The other end of the first tube 130 is connected to the output of the first pump 122. In the same way, one end of the second tube 132 is connected to the second air communication port 26 of the reaction processing vessel 10. A packing material 136 or a seal for securing airtightness is preferably arranged at the junction of the second air communication port 26 and the end of the second tube 132. The other end of the second tube 132 is connected to the output of the second pump 124.

The first pump 122 and the second pump 124 may be, for example, micro blower pumps each comprising a diaphragm pump. As the first pump 122 and the second pump 124, for example, micro blower pumps (MZB1001 T02 model) manufactured by Murata Manufacturing Co., Ltd., or the like can be used. While this micro blower pump can increase the pressure on a secondary side to be higher than a primary side during operation, the pressure on the primary side and the pressure on the secondary side become equal at the moment when the pump is stopped or when the pump is stopped.

The CPU 105 controls the air supply and pressurization from the first pump 122 and the second pump 124 via the first pump driver 126 and the second pump driver 128. The air supply and pressurization from the first pump 122 and the second pump 124 act on the sample 50 inside the channel 12 through the first air communication port 24 and the second air communication port 26 and serves as a propulsive force to move the sample 50. More specifically, by alternately operating the first pump 122 and the second pump 124, the pressure applied to either end surface of the sample 50 becomes larger than the pressure applied to the other end, and a propulsive force relating to the movement of the sample 50 can thus be obtained. By alternately operating the first pump 122 and the second pump 124, the sample 50 can be moved in a reciprocating manner in the channel so as to be repeatedly exposed to each temperature region of the channel 12 of the reaction processing vessel 10. As a result, a thermal cycle can be applied to the sample 50. More specifically, target DNA in the sample 50 is selectively amplified by repeatedly applying a step of denaturation in the high temperature region and a step of annealing and elongation in the medium temperature region. In other words, the high temperature region can be considered to be a denaturation temperature region, and the medium temperature region can be considered to be an annealing and elongation temperature region. The time for staying in each temperature region can be appropriately set by changing the time during which the sample 50 stops at a predetermined position in each temperature region.

The reaction processor 100 according to the present embodiment is further provided with a fluorescence detector 140. As described above, a predetermined fluorescent probe is added to the sample 50. Since the intensity of a fluorescence signal emitted from the sample 50 increases as the amplification of the DNA proceeds, the intensity value of the fluorescence signal can be used as an index serving as a decision-making factor for the progress of the PCR or the termination of the reaction.

As the fluorescence detector 140, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 50 and thus allows an optimum optical and detection system for a sample having various characteristics to be provided. Further, the optical fiber-type fluorescence detector is suitable for detecting fluorescence from a sample existing in a small or narrow region such as a channel because of the small diameter of a ray of light brought by the optical fiber-type fluorescence detector.

The optical fiber-type fluorescence detector 140 is provided with an optical head 142, a fluorescence detector driver 144, and an optical fiber 146 connecting the optical head 142 and the fluorescence detector driver 144. The fluorescence detector driver 144 includes a light source for excitation light (LED, a laser, or a light source adjusted to emit other specific wavelengths), an optical fiber-type multiplexer/demultiplexer and a photoelectric conversion device (PD, APD, or a light detector such as a photomultiplier) (neither of which is shown), and the like and formed of a driver or the like for controlling these. The optical head 142 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 144 through the optical fiber 146 and converted into an electric signal by the photoelectric conversion element.

In the reaction processor 100 according to the present embodiment, the optical head 142 is arranged such that fluorescence from the sample 50 in the channel connecting the high temperature region and the medium temperature region can be detected. Since the reaction progresses while the sample 50 is repeatedly moved in a reciprocating manner in the channel such that predetermined DNA contained in the sample 50 is amplified, by monitoring a change in the amount of detected fluorescence, the progress of the DNA amplification can be learned in real time. Further, in the reaction processor 100 according to the present embodiment, an output value from the fluorescence detector 140 is utilized for controlling the movement of the sample 50, as described later. The fluorescence detector is not limited to an optical fiber-type fluorescence detector as long as the fluorescence detector exhibits the function of detecting fluorescence from a sample.

Figure 6:
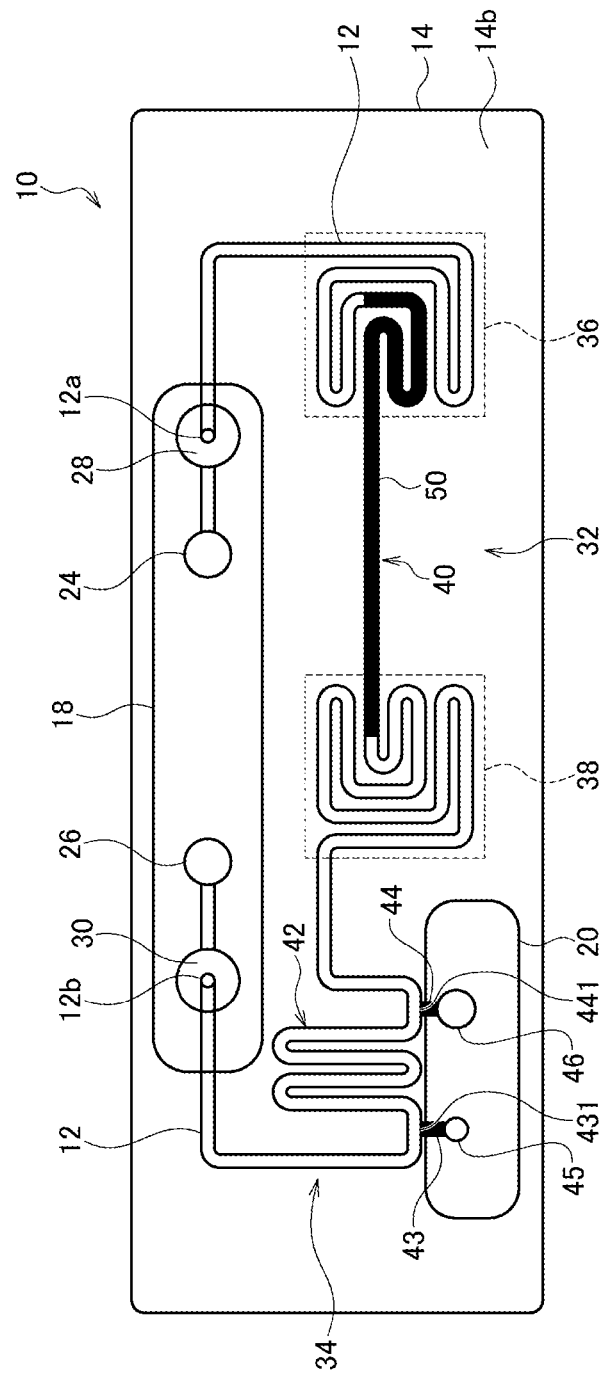
FIG. 6 is a diagram showing a state where a thermal cycle is applied to a sample inside a channel of the reaction processing vessel.

FIG. 6 is a diagram showing a state where a thermal cycle is applied to a sample inside a channel of the reaction processing vessel. In the reaction processing vessel 10 shown in FIG. 6, the sample 50 loaded into the dispensing channel 42 between the first branch point 431 and the second branch point 441 in the dispensing region 34 is moved to the thermal cycle region 32. More specifically, by setting the reaction processing vessel 10 filled with the sample 50 in the reaction processor 100 and operating only the second pump 124, the sample 50 in the dispensing region 34 is propelled to the thermal cycle region 32. Thereafter, as described above, by alternately operating the first pump 122 and the second pump 124 (see FIG. 5), the sample 50 is reciprocally moved in the channel 12 such that the sample 50 is continuously moved reciprocally between the high temperature region 36 and the medium temperature region 38, and a thermal cycle can be thereby applied to the sample 50.

Figure 7:
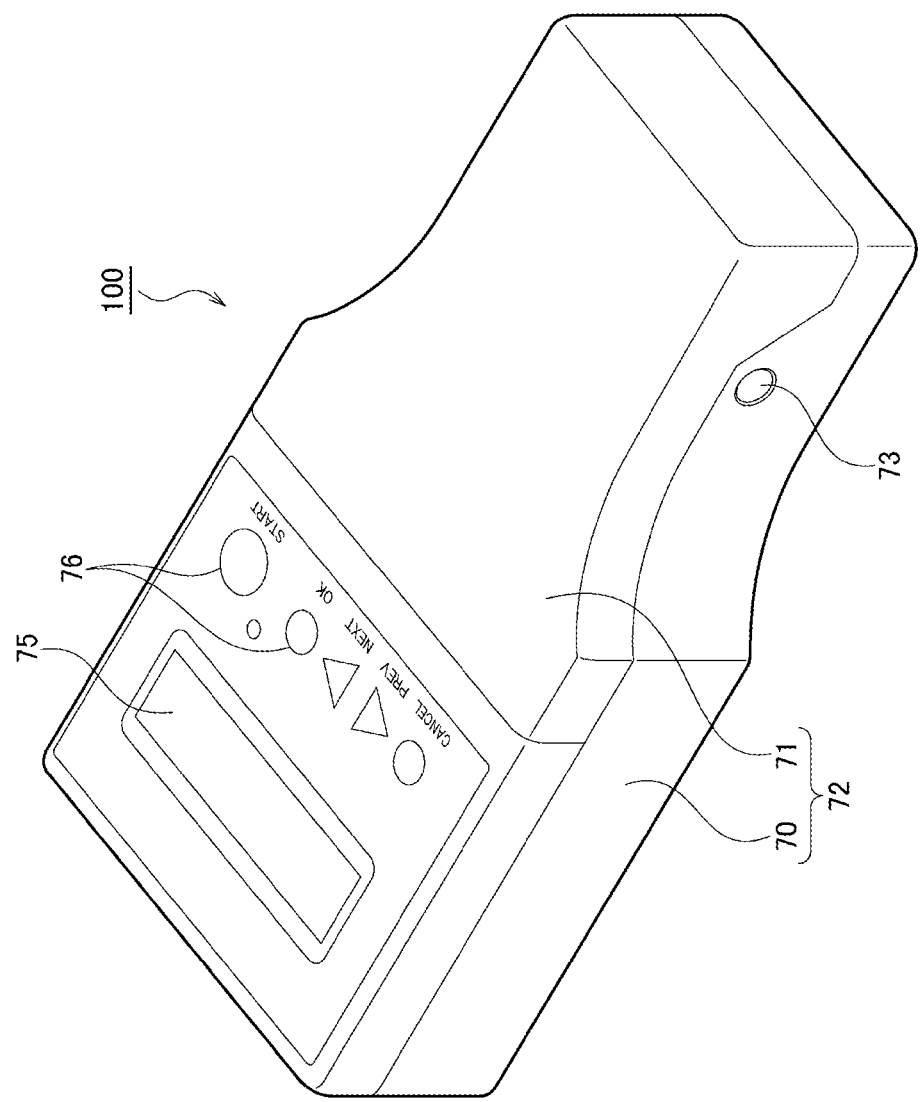
FIG. 7 is a diagram showing the exterior view of the reaction processor according to the embodiment of the present invention.

FIG. 7 is a diagram showing the exterior view of the reaction processor 100 according to the embodiment of the present invention. The reaction processor 100 according to the present embodiment is formed in such a manner that the reaction processor 100 is portable by the user. As shown in FIG. 7, the reaction processor 100 includes a housing 72 consisting of an approximately rectangular parallelepiped housing main unit 70 having an opening at a part of the upper surface thereof and of a cover portion 71 covering the opening of the housing main unit 70. The cover portion 71 is capable of being opened and closed with respect to the housing main unit 70. In the housing 72, many of the components of the reaction processing vessel 10 described in FIG. 5 are housed. Further, on the upper surface of the reaction processor 100, a display unit 75 for displaying an operation state of the reaction processor 100, the input display of a command, and the progress and result of PCR and an operation button 76 are arranged. Although not limited to this, a part of the shape of the reaction processor 100 is formed to be narrow so as to be easily held by the user.

Figure 8:
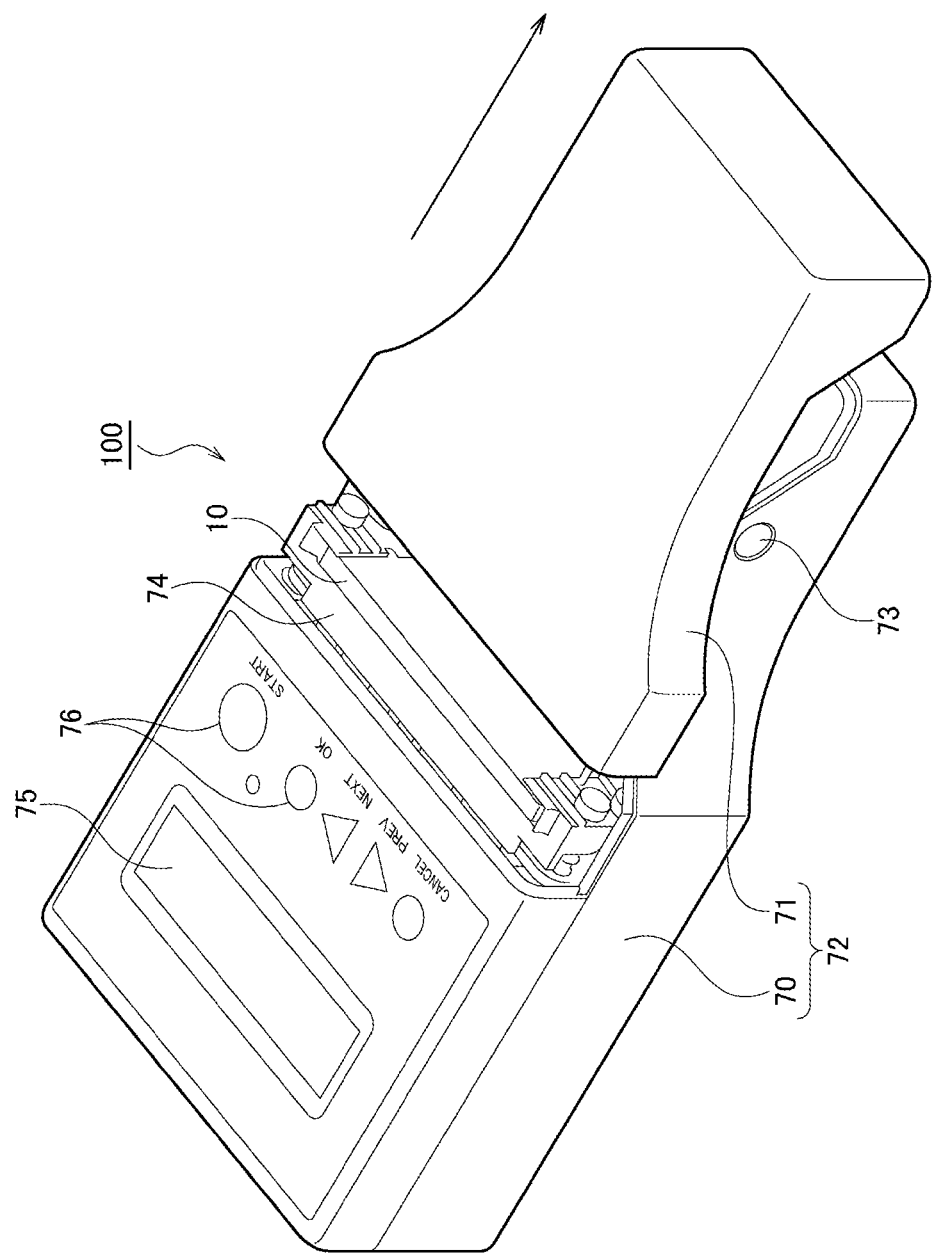
FIG. 8 is a diagram showing a state where a cover portion is open with respect to a housing main unit in the reaction processor according to the embodiment of the present invention.

FIG. 8 is a diagram showing a state where the cover portion 71 is open with respect to the housing main unit 70 in the reaction processor 100 according to the embodiment of the present invention. The cover portion 71 can be opened by sliding the cover portion 71 in the longitudinal direction (the direction of an arrow in FIG. 8, and, hereinafter, this direction is referred to as "downward direction of the housing 72" and the opposite direction is referred to as "upward direction of the housing 72") of the housing 72 while pressing a lock button 73 provided on the side surface of the housing main unit 70. As shown in FIG. 8, when the cover portion 71 is in the open state, the vessel installation unit 74 is exposed, which allows the reaction processing vessel 10 to be installed in the vessel installation unit 74 or removed from the vessel installation unit 74.

Figure 9:
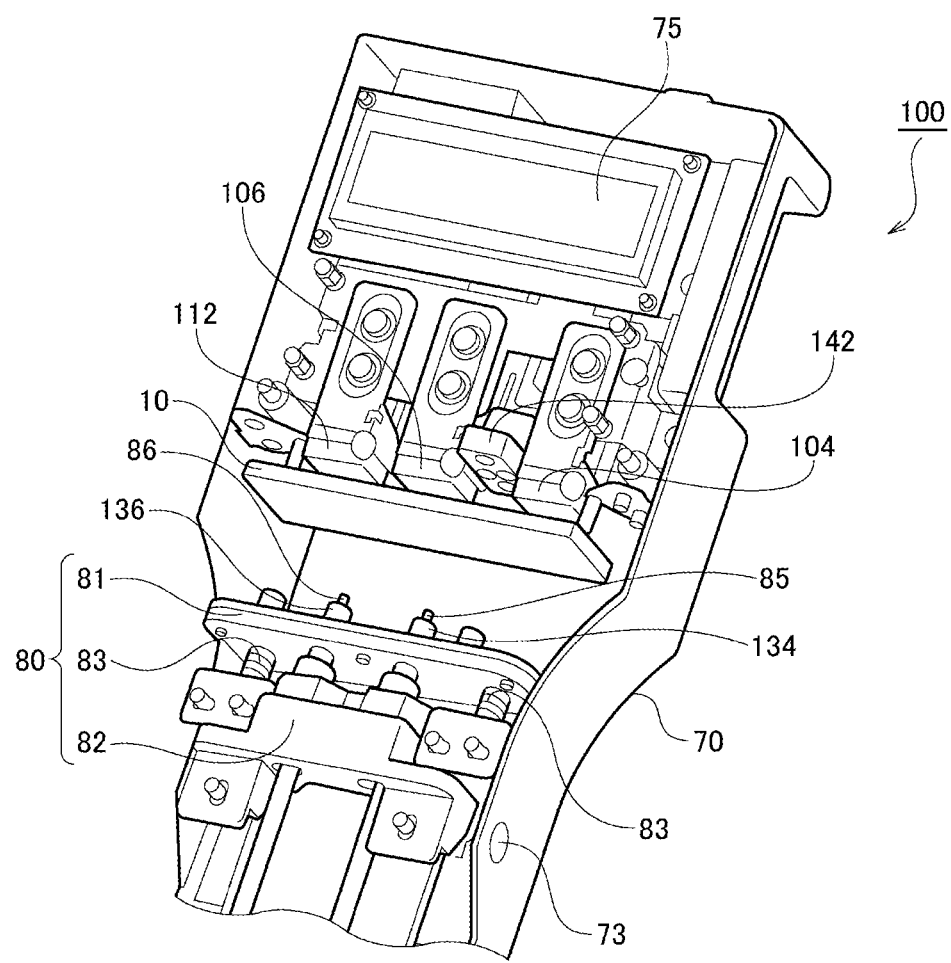
FIG. 9 is a perspective view for explaining the internal configuration of the reaction processor according to the embodiment of the present invention.

FIG. 9 is a perspective view for explaining the internal configuration of the reaction processor 100 according to the embodiment of the present invention. As shown in FIG. 9, the reaction processing vessel 10, the high temperature heater 104, the medium temperature heater 106, the optical head 142, and the like are housed in the housing main unit 70.

Figure 10:
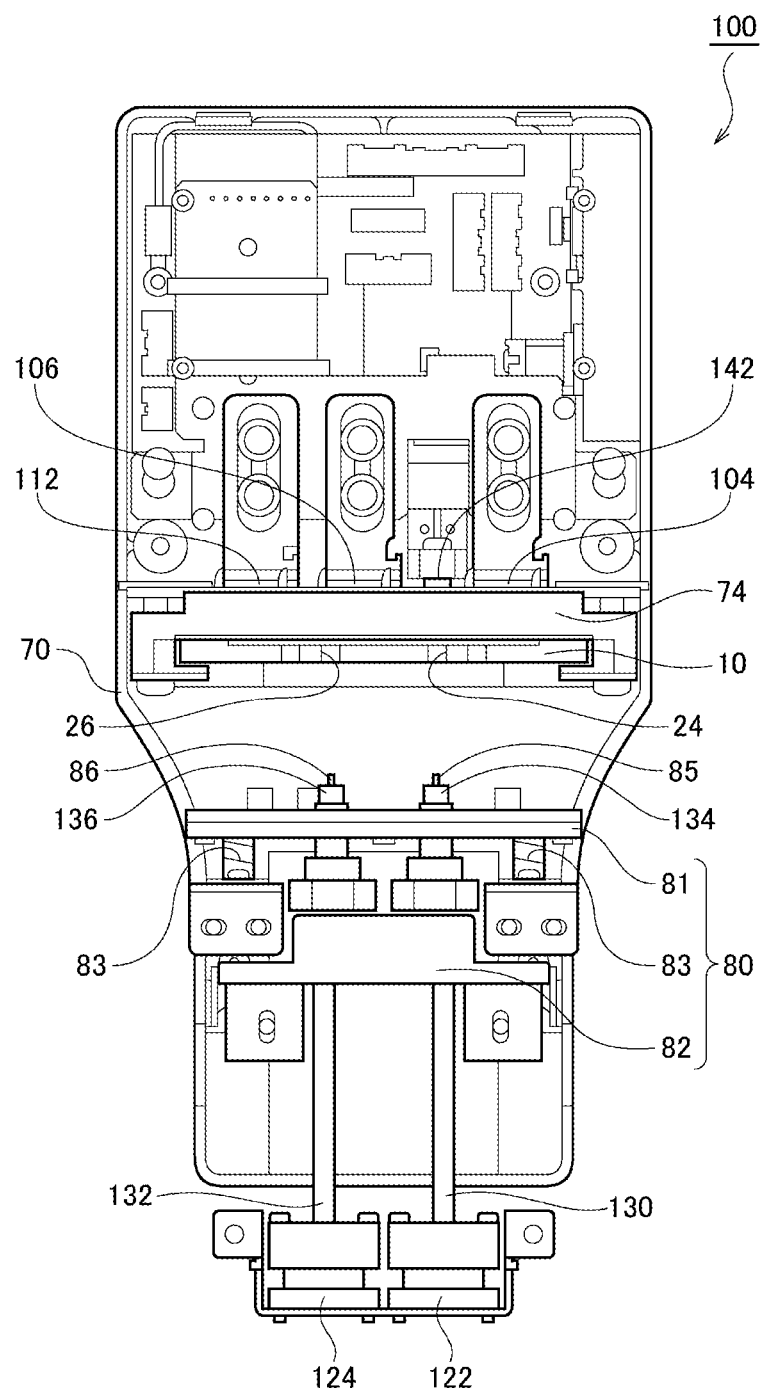
FIG. 10 is a diagram for explaining the reaction processor when the cover portion is in an open state.

FIG. 10 is a diagram for explaining the reaction processor 100 when the cover portion is in the open state and is a diagram showing the relationship of the reaction processing vessel 10 and the vessel installation unit 74 with other components in a more easily understandable manner.

As shown in FIG. 9 and FIG. 10, the reaction processing vessel 10 is installed in the vessel installation unit 74 such that the main surface thereof is orthogonal to the longitudinal direction of the housing main unit 70. Further, on one main surface side of the reaction processing vessel 10, the high temperature heater 104, the medium temperature heater 106, and the dispensing heater 112 are arranged. Further, on the other main surface side of the reaction processing vessel 10, a vessel alignment mechanism 80 for adjusting the position of the reaction processing vessel 10 is arranged.

Figure 11:
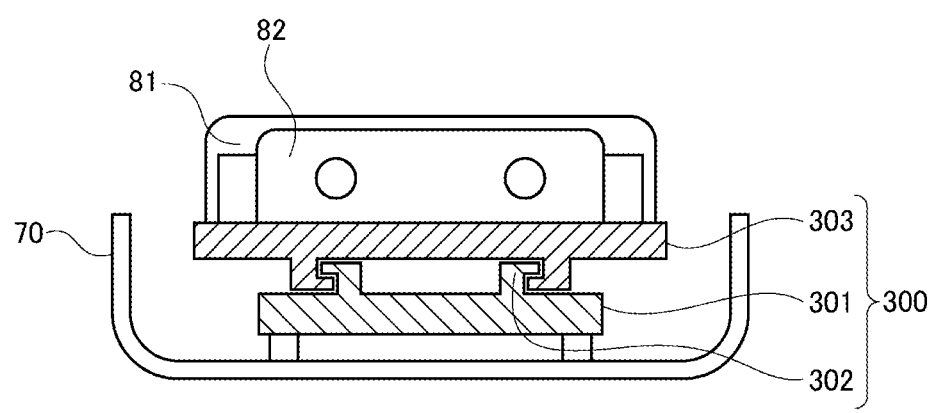
FIG. 11 is a diagram for explaining a slide mechanism of the reaction processor according to the embodiment of the present invention.

As shown in FIG. 10, the vessel alignment mechanism 80 includes a pressing member 81, a support 82, and a slide mechanism that are arranged facing the other main surface of the reaction processing vessel 10. FIG. 11 is a schematic cross-sectional view for explaining this slide mechanism 300 and shows a cross-sectional view when viewed in the upward direction of the slide mechanism 300 on a plane perpendicular to a rail 302 described later. The slide mechanism 300 includes a base plate 301 fixed to the housing main unit 70, a rail 302 formed on the base plate 301 and extending in the longitudinal direction of the housing main unit 70, and a slide plate 303 which moves on the rail 302. On the slide plate 303, the pressing member 81, the support 82, and the like are fixed. Further, since the cover portion 71 is fixed to the slide plate 303, the cover portion 71 can slide with respect to the housing main unit 70 to open and close the housing 72, and the pressing member 81, the support 82, and the like can also move in the longitudinal direction with respect to the housing main unit 70 along with the opening and closing of the cover portion 71.

Figure 12:
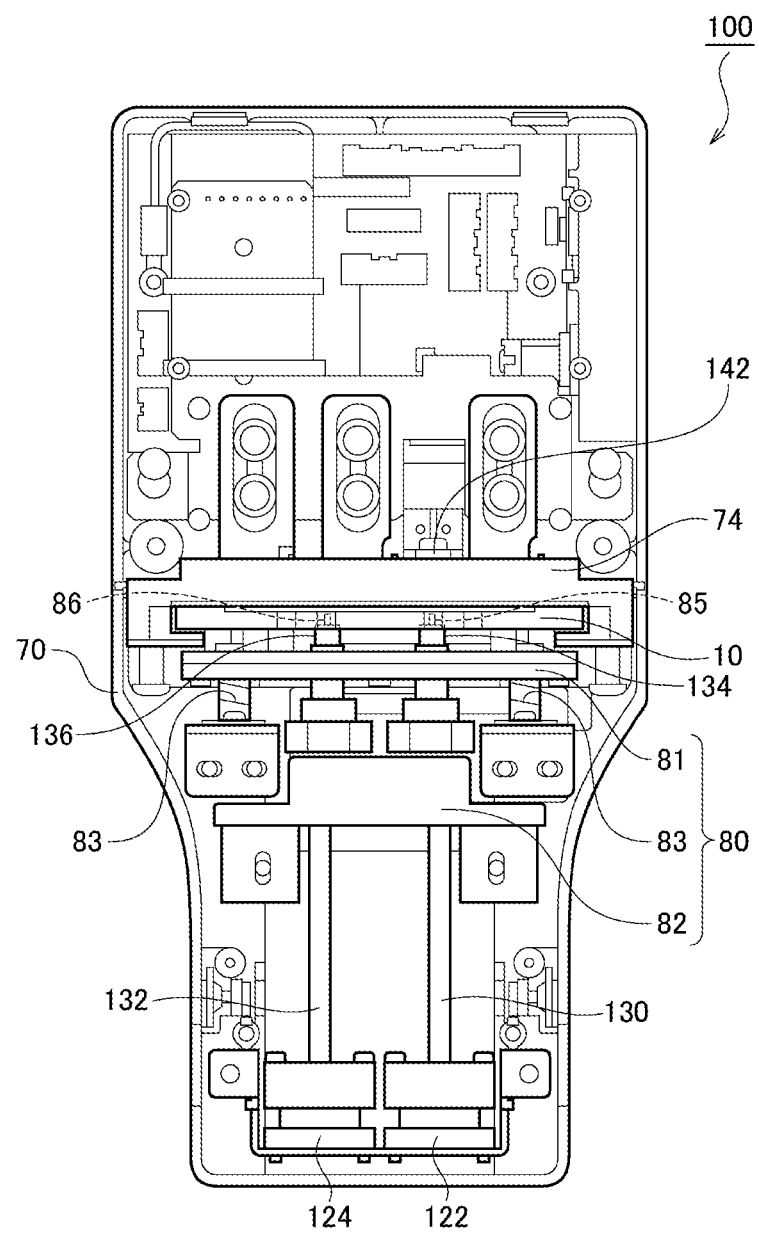
FIG. 12 is a diagram for explaining the reaction processor when the cover portion is in a closed state.

FIG. 12 is a diagram for explaining the reaction processor 100 when the cover portion 71 is in the closed state. As shown in FIG. 10, when the cover portion 71 is in the open state, the pressing member 81 and the support 82 move downward (that is, in a direction away from the reaction processing vessel 10). At this time, one main surface of the reaction processing vessel 10 is separated from the high temperature heater 104, the medium temperature heater 106, and the dispensing heater 112. On the other hand, as shown in FIG. 12, when the state of the cover portion 71 is changed from being in the open state to the closed state, the pressing member 81 and the support 82 move upward (that is, in the direction approaching the reaction processing vessel 10). The reaction processing vessel 10 is pushed by the pressing member 81 together with the vessel installation unit 74 and displaced upward, and the reaction processing vessel 10 substantially comes into surface-contact with the high temperature heater 104, the medium temperature heater 106, and the dispensing heater 112 (which do not appear due to the displacement of the vessel installation unit 74) illustrated in FIG. 10. This allows the reaction processing vessel 10 to be heated by the high temperature heater 104, the medium temperature heater 106, and the dispensing heater 112.

The vessel alignment mechanism 80 further includes an elastic member (for example, a spring) 83 that presses the pressing member 81 against the reaction processing vessel 10 when the cover portion 71 is in the closed state. By bringing the reaction processing vessel 10 into close contact with the high temperature heater 104, the medium temperature heater 106, and the dispensing heater 112 by the elastic member 83, the channel of the reaction processing vessel 10 can be maintained at a predetermined temperature without fail.

As shown in FIGS. 10 and 12, the vessel alignment mechanism 80 is equipped with a liquid feeding system including a first pump 122, a second pump 124, a first tube 130, and a second tube 132 via the support 82. The first pump 122 and the second pump 124 are arranged so as to slide in conjunction with the cover portion 71, the pressing member 81, and the support 82, and the first tube 130 and the second tube 132 extend in the upward direction of the housing 72 from the first pump 122 and the second pump 124, respectively. A first needle 85 and a second needle 86 that are hollow are provided at the respective ends of the first tube 130 and the second tube 132, respectively. The first needle 85 and the second needle 86 penetrate through the pressing member 81 and are exposed on the reaction processing vessel 10 side. Packing materials 134 and 136 for securing the above-mentioned airtightness are provided around the first needle 85 and the second needle 86 exposed on the reaction processing vessel 10 side.

As described above, when the state of the cover portion 71 is changed from the open state to the closed state, the pressing member 81, the support 82, and the like move in the direction approaching the reaction processing vessel 10, and the first tube 130 extending from the first pump 122 and the second tube 132 extending from the second pump 124 eventually communicate with the channel 12 of the reaction processing vessel 10. More specifically, when the pressing member 81 presses the reaction processing vessel 10, portions of the first sealing film 18 of the reaction processing vessel 10 are perforated by the first needle 85 and the second needle 86 such that the first needle 85 is connected to the first air communication port 24 of the reaction processing vessel 10 and that the second needle 86 is connected to the second air communication port 26 of the reaction processing vessel 10.

As shown in FIGS. 9, 10, and 12, the optical head 142 of the fluorescence detector is arranged between the high temperature heater 104 and the medium temperature heater 106 in the housing main unit 70. This is to detect fluorescence from a sample passing through the connection region between the high temperature region and the medium temperature region. In the present embodiment, when the state of the cover portion 71 is changed from the open state to the closed state such that the reaction processing vessel 10 comes into contact with the high temperature heater 104, the medium temperature heater 106, and the dispensing heater 112, a predetermined fluorescence detection point located in the connection region of the reaction processing vessel 10 is optimally aligned with the optical head 142.

The reaction processor 100 according to the present invention have been explained above. In the reaction processor 100 according to the present embodiment, the vessel alignment mechanism 80 is provided such that the reaction processing vessel 10 is aligned (i.e., brought into contact) with the high temperature heater 104, the medium temperature heater 106, and the dispensing heater 112 in conjunction with the state of the cover portion 71 being changed from the open state to the closed state. This allows the trouble of aligning the reaction processing vessel 10 to be avoided, and the workability in a reaction process through PCR can thus be improved.

Further, in the reaction processor 100 according to the present embodiment, the first tube 130 extending from the first pump 122 and the second tube 132 extending from the second pump 124 automatically communicate with the channel 12 of the reaction processing vessel 10 in conjunction with the state of the cover portion 71 being changed from the open state to the closed state. This allows the trouble of connecting the first tube 130 and the second tube 132 to the reaction processing vessel 10 to be avoided, and the workability in a reaction process through PCR can thus be further improved.

Further, in the reaction processor 100 according to the present embodiment, a predetermined fluorescence detection point of the reaction processing vessel 10 is automatically aligned with the optical head 142 of the fluorescence detector in conjunction with the state of the cover portion 71 being changed from the open state to the closed state. This allows the trouble of aligning the optical head 142 with the reaction processing vessel 10 to be avoided, and the workability in a reaction process through PCR can thus be further improved. Further, by providing a positioning hole in the reaction processing vessel 10 and providing a corresponding positioning pin in the reaction processor 100, it is also possible to improve the accuracy of the series of alignments. A plurality of such positioning hole and pin sets may be provided.

The operator puts the reaction processing vessel 10 contained with a sample in the reaction processor 100 having the above-described mechanism and closes the cover portion 71 so that tubes and the like that are connected to each heater and each pump become connected to the reaction processing vessel 10. Thereby, the preparation for a reaction process through PCR can be completed. Thereafter, the operator operates the operation button 76 to start the reaction process and continues monitoring or the like while checking the progress and the result of the reaction process displayed on the display unit 75 in real time. The amount of fluorescence detected by the fluorescence detector 140 may be displayed on the display unit 75. For example, for a specific sample, a threshold value of the amount of fluorescence may be determined in advance, and the reaction process may be stopped when the threshold value is exceeded. Alternatively, such a program may be implemented.

Figure 13:
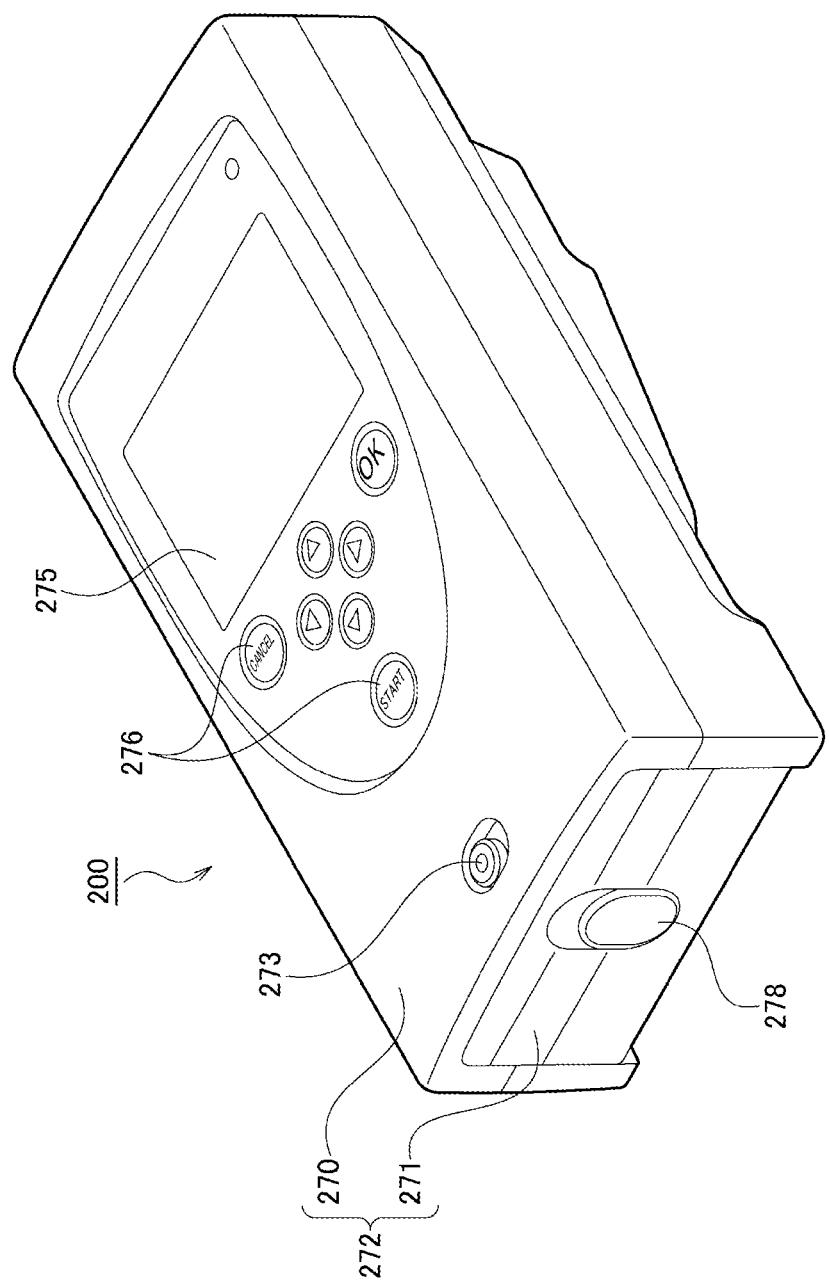
FIG. 13 is a diagram showing the exterior view of a reaction processor according to another embodiment of the present invention.
Figure 14:
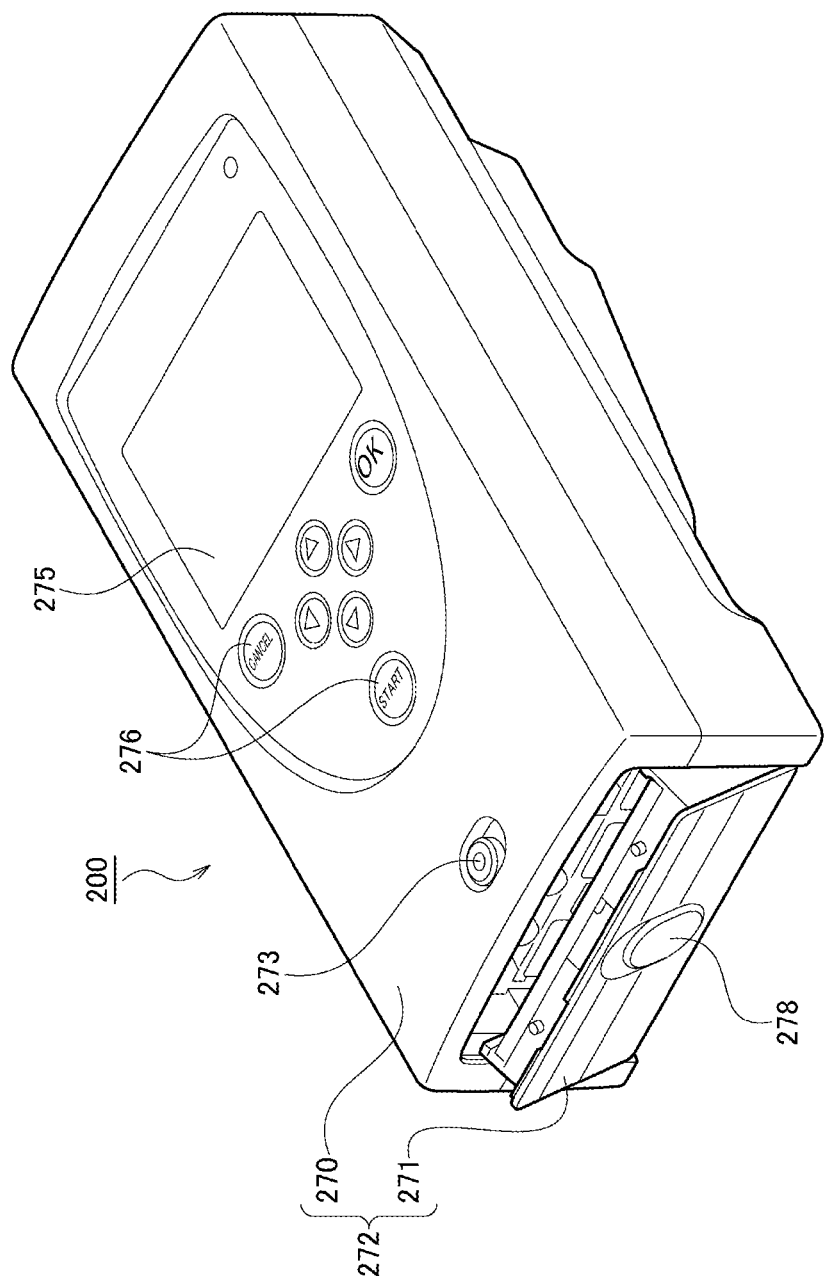
FIG. 14 is a diagram showing a state where a cover portion is open with respect to a housing main unit in the reaction processor according to the other embodiment of the present invention.

FIG. 13 and FIG. 14 are diagrams showing the exterior view of a reaction processor 200 according to another embodiment of the present invention. Descriptions of functions and configurations similar to those of the reaction processor 100 according to the previous embodiment will be omitted. The reaction processor 200 according to the present embodiment is also formed in such a manner that the reaction processor 200 is portable by the user. As shown in FIGS. 13 and 14, the reaction processor 200 includes a housing 272 consisting of an approximately rectangular parallelepiped housing main unit 270 having an opening at one end surface thereof in the longitudinal direction and of a cover portion 271 which covers the opening of the housing main unit 270 and is capable of being opened and closed. A display unit 275 and operation buttons 276 are arranged on the upper surface of the reaction processor 200.

FIG. 13 shows the reaction processor 200 when the cover portion 271 is in the closed state, and FIG. 14 shows the reaction processor 200 when the cover portion 271 is in the open state. The cover portion 271 can be maintained to be in the closed state by, for example, a lock mechanism (not shown) and can be opened by sliding a slide lock switch 273 to release the lock of the lock mechanism. Further, in the open state, the reaction processing vessel 10 can be easily detached from the reaction processor 200 by sliding a reaction processing vessel removal slide switch 278 in the upper surface direction.

Figure 15:
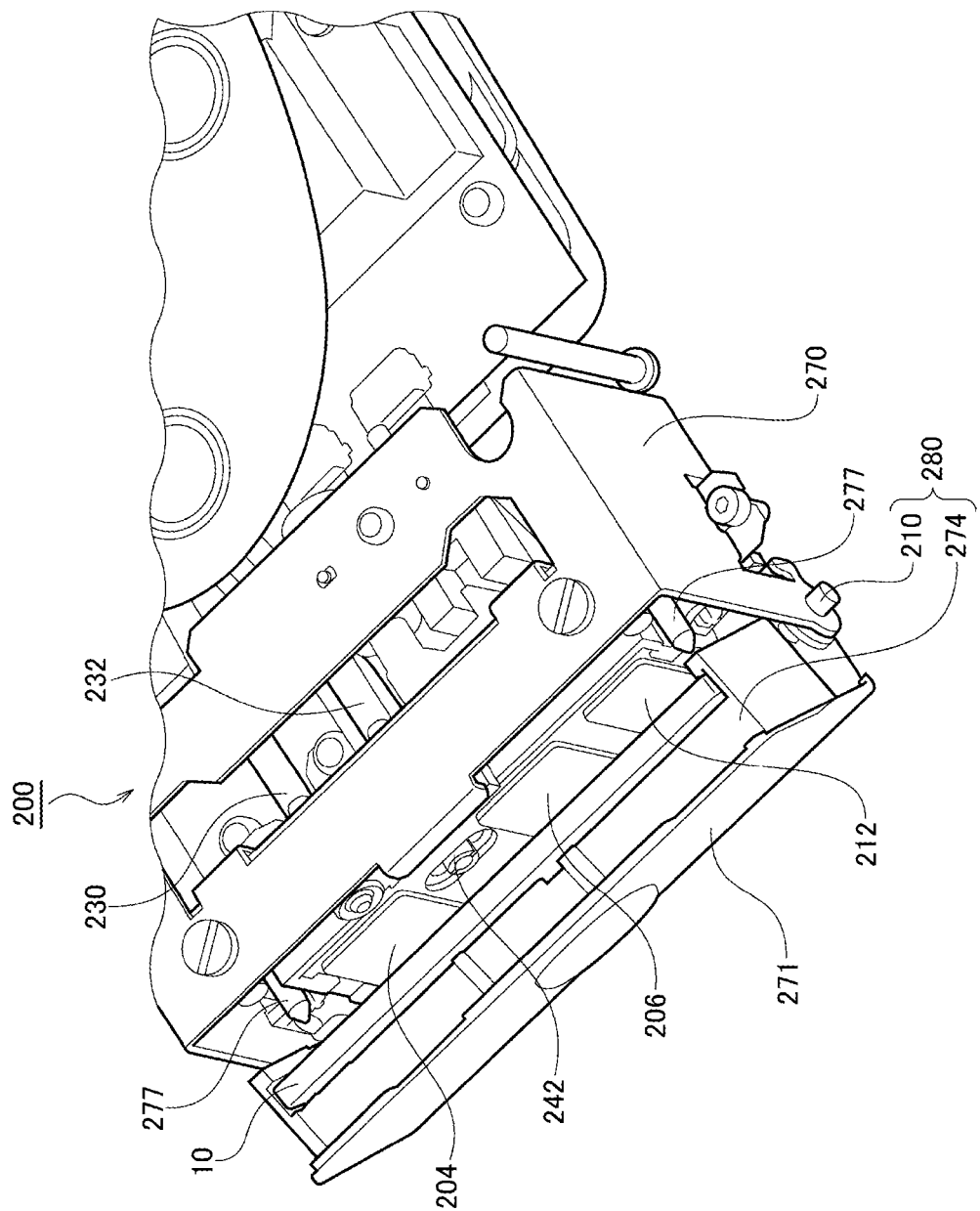
FIG. 15 is a diagram for explaining the reaction processor according to the other embodiment of the present invention.

FIG. 15 is a diagram transparently showing a structure near the cover portion 271 of the reaction processor 200 for easy understanding. The cover portion 271 is capable of being opened and closed with respect to the housing main unit 270 by a hinge mechanism described later. As shown in FIG. 15, a high temperature heater 204, a medium temperature heater 206, a dispensing heater 212, an optical head 242, an end portion of a first tube 230 extending from a first pump (not shown), and an end portion of a second tube 232 extending from a second pump (not shown) are arranged at the opening of the housing main unit 270 on the housing main unit 270 side. Further, a vessel alignment mechanism 280 is arranged on the cover portion 271 so as to face the heaters.

In conjunction with the state of the cover portion 271 being changed from the open state to the closed state, the vessel alignment mechanism 280 aligns the reaction processing vessel 10 so that the reaction processing vessel 10 can be heated by the high temperature heater 204, the medium temperature heater 206, and the dispensing heater 212. The vessel alignment mechanism 280 includes a vessel installation unit 274 for arranging the reaction processing vessel 10 inside the cover portion 271, and a hinge mechanism 210 which allows the cover portion 271 to be opened and closed.

In the reaction processor 200 shown in FIG. 15, in a state where the reaction processing vessel 10 is installed in the vessel installation unit 274, the state of the cover portion 271 is changed from the open state to the closed state by the hinge mechanism 210, and the closed state is maintained by a lock mechanism (not shown). At this time, the reaction processing vessel 10 is automatically aligned with the high temperature heater 204, the medium temperature heater 206, and the dispensing heater 212. An elastic member (not shown) is provided in the vessel alignment mechanism 280 so that the reaction processing vessel 10 is in close contact with each heater at this time. At the same time, the end portion of the first tube 230 and the end portion of the second tube 232 automatically communicate with the channel 12 of the reaction processing vessel 10, and the predetermined fluorescence detection point of the reaction processing vessel 10 is automatically aligned with the optical head 242 of the fluorescence detector. Further, by providing a positioning hole in the reaction processing vessel 10 and providing a corresponding positioning pin 277 in the reaction processor 200, the accuracy of the series of alignments is improved. As described, the reaction processor 200 according to the present embodiment also allows the workability in a reaction process through PCR to be further improved. According to an alignment mechanism provided with such a hinge mechanism, a part that moves and the range of the part can be reduced, and the reliability of the device can thus be improved.

Further, in this embodiment, functional components (elements) such as the high temperature heater 204, the medium temperature heater 206, the dispensing heater 212, the end portion of the first tube 230, the end portion of the second tube 232, and the optical head 242 of the fluorescence detector are arranged one-sidedly on one principal surface of the reaction processing vessel 10. This allows the mechanical parts and the like of the reaction processor 200 to be collectively arranged on one side of the reaction processing vessel 10 and thus allows for the simplification of the mechanism design and the downsizing of the device.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

What is claimed is:

1. A PCR method comprising:
   preparing a reaction processing vessel provided with a channel with air communication ports at both ends;
   introducing a sample into the channel;
   preparing a reaction processor including:
   a vessel installation unit for installing the reaction processing vessel;
   a heater for maintaining a part of the channel at a plurality of temperatures;
   a pump for moving the sample in the channel; and
   a cover portion that makes the vessel installation unit accessible by opening the cover portion;
   opening the cover portion and setting the reaction processing vessel in the vessel installation unit of the reaction processor;
   closing the cover portion and housing the reaction processing vessel in the reaction processor, thereby bringing the reaction processing vessel into close contact with the heater and connecting the pump to the air communication ports;
   maintaining the part of the channel at the plurality of temperatures; and
   moving the sample between a plurality of temperature regions in a reciprocating manner by operating the pump and stopping the sample in a temperature region by stopping the pump.

2. The PCR method according to claim 1, wherein the pump has a primary side at an inlet to the pump and a secondary side at an outlet of the pump; and wherein a pressure on the primary side and a pressure on the secondary side become equal in the pump when the pump is stopped.

3. The PCR method according to claim 1, wherein the plurality of temperature regions include a denaturation temperature region for causing denaturation of DNA in the sample and an annealing and elongation temperature region for causing annealing and elongation of DNA in the sample.

4. The PCR method according to claim 1, wherein the reaction processor further includes a fluorescence detector for detecting fluorescence emitted from the sample passing inside the channel connecting the plurality of temperature regions.

5. The PCR method according to The PCR method according to wherein the reaction processing vessel includes a sealing film for sealing the air communication ports; and wherein the pump includes tubes for connecting the air communication ports and a hollow needle provided at the tip of each of the tubes, and further comprising: perforating the sealing film with the hollow needles so as to cause the pump and the channel to communicate with each other.

\* \* \* \* \*